(12) United States Patent
Yang et al.

(10) Patent No.: US 11,311,599 B2
(45) Date of Patent: Apr. 26, 2022

(54) β-1,3-GLUCAN-PEPTIDE COMPLEX: COMPOSITIONS AND METHODS

(71) Applicant: Quegen Biotech Co., Ltd., Gyeonggi-do (KR)

(72) Inventors: Chul Su Yang, Gyeonggi-do (KR); Byeong Hee Park, Gyeonggi-do (KR); Je Kyoung Kim, Gyeonggi-do (KR); Yong Man Jang, Gyeonggi-do (KR); Soo Dong Kim, Seoul (KR); Min Ji Kim, Gyeonggi-do (KR)

(73) Assignee: Quegen Biotech Co., Ltd., Gyeonggi-do (KR)

( * ) Notice: Subject to any disclaimer, the term of this patent is extended or adjusted under 35 U.S.C. 154(b) by 0 days.

(21) Appl. No.: 17/254,234

(22) PCT Filed: Jun. 19, 2019

(86) PCT No.: PCT/KR2019/007374
§ 371 (c)(1),
(2) Date: Dec. 18, 2020

(87) PCT Pub. No.: WO2019/245275
PCT Pub. Date: Dec. 26, 2019

(65) Prior Publication Data
US 2021/0268060 A1    Sep. 2, 2021

(30) Foreign Application Priority Data
Jun. 20, 2018 (KR) .................. 10-2018-0070846

(51) Int. Cl.
*A61K 38/10* (2006.01)
*A23L 33/18* (2016.01)
(Continued)

(52) U.S. Cl.
CPC .............. *A61K 38/10* (2013.01); *A23L 33/18* (2016.08); *A61K 45/06* (2013.01); *A61P 31/00* (2018.01)

(58) Field of Classification Search
CPC ......... A23L 33/18; A61P 31/00; A61K 38/10; A61K 45/06
See application file for complete search history.

(56) References Cited

U.S. PATENT DOCUMENTS

2016/0208260 A1    7/2016 Ishii et al.

FOREIGN PATENT DOCUMENTS

| JP | 2009-280513 | 12/2009 |
|---|---|---|
| KR | 10-0241264 | 3/2000 |

(Continued)

OTHER PUBLICATIONS

Kim et al., "The targeted delivery of the c-Src peptide complexed with schizophyllan to macrophages inhibits polymicrobial sepsis and ulcerative colitis in mice," Biomaterials (2016) 89:1-13.

(Continued)

*Primary Examiner* — Kevin S Orwig
*Assistant Examiner* — John Michael Cronin
(74) *Attorney, Agent, or Firm* — Morrison & Foerster LLP

(57) ABSTRACT

The present invention relates to a composition for use in preventing, alleviating, or treating inflammatory disease, or an anti-inflammatory composition, which comprises: β-1,3-glucan; and the peptide composed of the amino acid sequence of SEQ ID NO: 4. The present invention also relates to an antibacterial composition against bacteria causative of sepsis, which comprises: β-1,3-glucan; the peptide composed of the amino acid sequence of SEQ ID NO: 4; and an antibiotic. The present invention also relates to a method for preventing or treating an inflammatory disease, the method comprising a step of administering β-1,3-glucan; and the peptide composed of the amino acid sequence of SEQ ID NO: 4 to a patient. Accordingly, when β-1,3-glucan and a peptide consisting of an amino acid sequence of SEQ ID NO: 4 are included, since the level of reactive oxygen species (ROS), sepsis-causing bacteria or an inflammatory cytokine of a sepsis mouse can be lowered, and the survival rate of the mouse can be significantly increased, they are effective for use in a composition or method for preventing, alleviating or treating an inflammatory disease such as sepsis. Particularly, the ROS generated by a phagocyte is specifically reduced and when used in combination with an antibiotic, ROS, sepsis-causing bacteria or the expression level of an inflammatory cytokine can be significantly (Continued)

decreased, thereby significantly increasing a survival rate, resulting in a more excellent effect.

20 Claims, 6 Drawing Sheets

Specification includes a Sequence Listing.

(51) Int. Cl.
*A61P 31/00* (2006.01)
*A61K 45/06* (2006.01)

(56) References Cited

FOREIGN PATENT DOCUMENTS

KR 10-2016-0140472 12/2016
KR 10-2017-0089766 8/2017

OTHER PUBLICATIONS

Mochizuki et al., "Immunization with antigenic peptides complexed with β-glucan induces potent cytotoxic T-lymphocyte activity in combination with CpG-ODNs," J Controlled Release (2015) 220:495-502.
Takedatsu et al., "A New Therapeutic Approach Using a Schizophyllan-based Drug Delivery System for Inflammatory Bowel Disease," Mol Ther (2012) 20(6):1234-1241.

```
                                                        SH3-2
                    SH3-1
Src    83 - GGVTTF ALYDYESRTETDLSFKKG RLQIVNNTEG DWWLAHSLSTGQTGYIPSNYV APSDS - 146
p67phox 456 - KKGSQVEALFSYEATQPEDLEFQEGDIILVLSKVNEEWLEG—ECKGKVGIFPKVFVEDCAT - 517
p47phox 160 - MAAPRAEALFDFTGNSKLELNFKAGDVIFLLSRINKDWLEG—TVRGATGIFPLSFVKILKD - 230
```

FIG. 1

SEQUENCE LISTING

<160> NUMBER OF SEQ ID NOS: 5

<210> SEQ ID NO 1

-continued

```
<211> LENGTH: 62
<212> TYPE: PRT
<213> ORGANISM: Artificial Sequence
<220> FEATURE:
<223> OTHER INFORMATION: c-Src

<400> SEQUENCE: 1

Gly Gly Val Thr Thr Phe Val Ala Leu Tyr Asp Thr Glu Ser Arg Thr
1               5                   10                  15

Glu Thr Asp Leu Ser Phe Lys Lys Gly Glu Arg Leu Gln Ile Val Asn
            20                  25                  30

Asn Thr Glu Gly Asp Trp Trp Leu Ala His Ser Leu Ser Thr Gly Gln
        35                  40                  45

Thr Gly Tyr Ile Pro Ser Asn Tyr Val Ala Pro Ser Asp Ser
    50                  55                  60

<210> SEQ ID NO 2
<211> LENGTH: 18
<212> TYPE: PRT
<213> ORGANISM: Artificial Sequence
<220> FEATURE:
<223> OTHER INFORMATION: SH3-1

<400> SEQUENCE: 2

Ala Leu Tyr Asp Tyr Glu Ser Arg Thr Glu Thr Asp Leu Ser Phe Lys
1               5                   10                  15

Lys Gly

<210> SEQ ID NO 3
<211> LENGTH: 20
<212> TYPE: PRT
<213> ORGANISM: Artificial Sequence
<220> FEATURE:
<223> OTHER INFORMATION: SH3-2

<400> SEQUENCE: 3

Trp Trp Leu Ala His Ser Leu Ser Thr Gly Gln Thr Gly Tyr Ile Pro
1               5                   10                  15

Ser Asn Tyr Val
            20

<210> SEQ ID NO 4
<211> LENGTH: 19
<212> TYPE: PRT
<213> ORGANISM: Artificial Sequence
<220> FEATURE:
<223> OTHER INFORMATION: SH3

<400> SEQUENCE: 4

Ala Leu Leu Ser Phe Lys Lys Gly Gly Gln Thr Gly Tyr Ile Pro Ser
1               5                   10                  15

Asn Tyr Val

<210> SEQ ID NO 5
<211> LENGTH: 19
<212> TYPE: PRT
<213> ORGANISM: Artificial Sequence
<220> FEATURE:
<223> OTHER INFORMATION: SC
```

```
<400> SEQUENCE: 5

Tyr Asp Tyr Glu Ser Arg Thr Glu Thr Asp Trp Trp Leu Ala His Ser
1               5                   10                  15

Leu Ser Thr
```

β-1,3-GLUCAN-PEPTIDE COMPLEX: COMPOSITIONS AND METHODS

CROSS REFERENCE TO RELATED APPLICATIONS

This application is a national stage application under 35 U.S.C. § 371 of International Application No. PCT/KR2019/007374, filed internationally on Jun. 19, 2019, which claims priority to and the benefit of Korean Patent Application No. 10-2018-0070846, filed on Jun. 20, 2018, the disclosures of which are incorporated herein by reference in their entirety.

INCORPORATION BY REFERENCE OF SEQUENCE LISTING

The present application is being filed along with a Sequence Listing in electronic format. The Sequence Listing is provided as a file entitled 717572003000SeqList.txt, created Dec. 18, 2020, which is 2.10 kilobytes in size. The information in the electronic format of the Sequence Listing is incorporated by reference in its entirety.

TECHNICAL FIELD

The present invention relates to a composition or antiinflammatory composition, which includes: β-1,3-glucan; and a peptide consisting of an amino acid sequence of SEQ ID NO: 4, for preventing, alleviating or treating an inflammatory disease.

The present invention also relates to an antibacterial composition against sepsis-causing bacteria, which includes: β-1,3-glucan; a peptide consisting of an amino acid sequence of SEQ ID NO: 4; and an antibiotic.

The present invention also relates to a method of preventing or treating an inflammatory disease, which includes administering β-1,3-glucan and a peptide consisting of an amino acid sequence of SEQ ID NO: 4 to a patient.

BACKGROUND ART

Excessive inflammatory responses caused by reactive oxygen species (ROS) may cause various inflammatory diseases including sepsis. Sepsis is an inflammatory response caused by excessive activation of the body's immune system when the living body is infected with pathogenic gram-negative bacteria and a lipopolysaccharide (LPS), which is a component of the cell wall, functions as a toxin, and may result in inflammation throughout the body or may be accompanied by shock when symptoms are severe. Recently, the importance of a c-Src-mediated acute inflammatory response in sepsis-associated acute lung injury has been revealed.

There are two main causes of ROS occurring in the body, such as mitochondrial respiration and phagocytosis mediated by phagocytes.

The degradation of substances absorbed by phagocytosis mediated by phagocytes is caused by a protease, and promoted by the so-called oxidative burst. This involves the production of ROS and nitric oxide (NO). Nicotinamide adenine dinucleotide phosphate (NADPH) oxidase (NOX) present in the membrane of a phagocyte reduces oxygen ($O_2$) to a superoxide anion ($O_2^-$). This induces the formation of hydrogen peroxide ($H_2O_2$) and the formation of highly reactive hydroxyl radicals through the Fenton reaction or hydrochlorite synthesis by a myeloperoxidase. In addition, peroxynitrite generated by the reaction between ROS and NO is a very effective antibacterial along with hypochlorite. These reactive species are called reactive oxygen or nitrogen species.

ROS (mtROS) generated by the respiration of mitochondria plays an important role in various innate immune signaling pathways. It activates a NOX or NLRP3 inflammasome and are involved in synthesis of inflammatory cytokines. In addition, mtROS is known to increase macrophage-mediated phagocytosis. The generation of mtROS is known to be regulated by diatomic gas mediators such as NO and carbon monooxide (CO).

NOX is a complex consisting of flavocytochrome b components (gp91phox/NOX2 and p22phox) and four cytosol proteins (p47phox, p67phox, p40phox, and Rac1/2) of a phagocyte. To activate the NOX complex, it is necessary to phosphorylate p47phox present at several serine residues. Besides this, binding of p22phox with several regulatory partners is essential, and as regulatory partners, there are NOX organizer 1 (NOXO1) which is the same as p47phox, NOX activator 1 (NOXA1) which is the same as p67phox, and Rac1 GTPase. Specific targeting of NOX playing a critical role in ROS production may bring a therapeutic effect in a lethal disease. Research of the above-mentioned signaling molecule may help in specific targeted therapeutic development. Partial, small chemical (non-peptide) inhibitors of NOX (diphenylene iodonium, 4-hydroxy-3-methoxyacetophenone-substituted, phenylarsine oxide and 4-(2-aminoethyl)-benzenesulfonyl fluoride) have been used in the inhibition of ROS production. However, since they have no specificity, they also inhibit enzymes which are similar or unrelated to NOX.

Schizophyllan (SPG) obtained from soluble β-glucan of *Schizophyllum commune* is a β-(1-3)-glucan-type polysaccharide. It forms a triple helix in a neutral solution. When the alkaline solution of SPG is neutralized, it is transformed into a single chain and returns to the original triple helix through a hydrophobic interaction and hydrogen bonding.

During such a physicochemical interaction, a stoichiometric complex is formed by bonding of two main chain glucoses, β-(1-3)-glucans, and one oligonucleotide (ODN) base or peptide. By using this complex, a SPG-based drug delivery system was designed to deliver functional ODN to target cells.

Korean Unexamined Patent Application No. 10-2016-0140472 relates to a bioconversion product of Sichuan pepper produced by microbial fermentation and enzyme-treated bioconversion, and discloses that the microbe may be *Schizophyllum commune*, and when the bioconversion product of Sichuan pepper is used as an active ingredient, the bioconversion product can be used as a pharmaceutical composition for preventing or treating sepsis. However, research on a complex of β-glucan such as SPG and a peptide and a method using the complex and an antibiotic has not been conducted.

DISCLOSURE

Technical Problem

Therefore, as a result of efforts to provide a composition effective against an inflammatory disease such as sepsis by specifically targeting NADPH oxidase playing a critical role in reactive oxygen species (ROS) production, when a type of β-glucan, which is a β-glucan-peptide complex prepared by binding of schizophyllan (SPG) and a specific peptide, and an antibiotic are used in combination, it significantly increases the survival rate of mice in which sepsis is induced by cecal ligation and puncture (CLP) and reduces a level of ROS, sepsis-causing bacteria or an inflammatory cytokine, so that it can be used in prevention, alleviation or treatment of an inflammatory disease such as sepsis. Thus, the present invention was completed.

Accordingly, the present invention is directed to providing a composition or antiinflammatory composition, which includes: β-1,3-glucan; and a peptide consisting of an amino acid sequence of SEQ ID NO: 4, for preventing, alleviating or treating an inflammatory disease.

The present invention is also directed to providing an antibacterial composition against sepsis-causing bacteria, which includes: β-1,3-glucan; a peptide consisting of an amino acid sequence of SEQ ID NO: 4; and an antibiotic.

The present invention is also directed to providing a method of preventing or treating an inflammatory disease, which includes administering β-1,3-glucan and a peptide consisting of an amino acid sequence of SEQ ID NO: 4 to a patient.

Technical Solution

To attain the above-described objects, the present invention may provide a composition or antiinflammatory composition, which includes: β-1,3-glucan; and a peptide consisting of an amino acid sequence of SEQ ID NO: 4, for preventing, alleviating or treating an inflammatory disease.

According to an exemplary embodiment of the present invention, the β-1,3-glucan and the peptide may be linked by a spacer.

According to an exemplary embodiment of the present invention, the space may be a peptide including a GGGG amino acid sequence.

According to an exemplary embodiment of the present invention, the β-1,3-glucan may be schizophyllan (SPG).

According to an exemplary embodiment of the present invention, the composition may further include an antibiotic.

According to an exemplary embodiment of the present invention, the antibiotic may be one or more selected from the group consisting of cephalosporins, β-lactam antibiotics, β-lactam/β-lactamase inhibitor antibiotics, quinolone antibiotics, glycopeptide antibiotics, carbapenem antibiotics, aminoglycoside antibiotics, macrolide antibiotics, monobactam antibiotics, sulfa drug antibiotics, aztreonam, clindamycin, tigecycline, colistin sodium methanesulfonate, metronidazole and spiramycin.

According to an exemplary embodiment of the present invention, the cephalosporins may include one or more selected from the group consisting of cefazolin, cefcapene pivoxil, cefpodoxime proxetil, cephradine, ceftriaxone, cefbuperazone, cefotaxime, cefminox, ceftazidime, cefpirome, cefixime, cephalexin, cefdinir, cefroxadine, cefuroxime, cefadroxil, cefoxitin, cefetamet pivoxil, ceftizoxime, cefamandole nafate, cefazedone, cefteram pivoxil, ceftezole, cefprozil, cefotetan, cefmenoxime, cefditoren pivoxil, cefatrizine propylene glycol, cefotiam, cefotiam hexetil hydrochloride, ceftibuten, cefaclor, cefoperazone, cefpiramide, cephalothin, cefodizime, cefonicid, cefmetazole and cefepime;

the β-lactam antibiotics may include one or more selected from the group consisting of nafcillin, piperacillin and ampicillin;

the β-lactamase inhibitor antibiotics may include any one or more selected from the group consisting of sulbactam, tazobactam, sultamicillintosylate, amoxicillin, potassium clavulanate, ticarcillin and pivoxyl sulbactam;

the quinolone antibiotics may include any one or more selected from the group consisting of ciprofloxacin, moxifloxacin, levofloxacin and lomefloxacin;

the glycopeptide antibiotics may include any one or more selected from the group consisting of vancomycin, linezolid and teicoplanin;

the carbapenem antibiotics may include any one or more selected from the group consisting of meropenem, doripenem monohydrate, cilastatin and imipenem monohydrate;

the aminoglycoside antibiotics may include any one or more selected from the group consisting of amikacin, tobramycin, netilmicin, sisomicin, isepamicin, fosfomycin and gentamicin;

the macrolide antibiotics may include any one or more selected from the group consisting of clarithromycin, roxithromycin and azithromycin; and the sulfa drug antibiotics may include any one or more selected from the group consisting of sulfamethoxazole and trimethoprim.

According to an exemplary embodiment of the present invention, the composition may reduce ROS production of one or more phagocytes selected from the group consisting of a macrophage, a dendritic cell, a monocyte, a mast cell, and a neutrophil.

According to an exemplary embodiment of the present invention, the inflammatory diseases may include any one or more selected from the group consisting of sepsis, septic shock, inflammatory bowel disease (IBD), peritonitis, nephritis, acute bronchitis, chronic bronchitis, osteoarthritis, bowel disease spondylitis, chronic obstructive pulmonary disease (COPD), rheumatoid arthritis, acute lung injury and broncho-pulmonary dysplasia.

According to an exemplary embodiment of the present invention, the method may further include administering an antibiotic to a patient.

The present invention may also provide a health functional food composition, which includes β-1,3-glucan; and a peptide consisting of an amino acid sequence of SEQ ID NO: 4 for preventing or alleviating an inflammatory disease.

The present invention may also provide an antiinflammatory composition, which includes β-1,3-glucan; and a peptide consisting of an amino acid sequence of SEQ ID NO: 4.

The present invention may also provide an antibacterial composition against sepsis-causing bacteria, which includes β-1,3-glucan; a peptide consisting of an amino acid sequence of SEQ ID NO: 4; and an antibiotic.

Hereinafter, the present invention will be described in further detail.

As described above, in a conventional art, NADHP oxidase (NOX) inhibitors were used to inhibit ROS, but they could not effectively inhibit ROS due to insufficient specificity. While there is a demand for development of a composition that specifically targets NOX and increases a therapeutic effect against an inflammatory disease such as sepsis, other than ROS, research on an effective composition that increases both of specificity and an antiinflammatory effect is still insignificant.

A composition according to the present invention, which includes β-1,3-glucan; and a peptide consisting of an amino acid sequence of SEQ ID NO: 4 significantly increases the survival rate of a subject infected by an inflammatory disease, reduces ROS, sepsis-causing bacteria or an expression level of an inflammatory cytokine, and more significantly increases its effect when used in combination with an antibiotic, therefore, it is effective in preventing, alleviating or treating an inflammatory disease.

Accordingly, the present invention provides a pharmaceutical composition for preventing or treating an inflammatory disease, which includes β-1,3-glucan; and a peptide consisting of an amino acid sequence of SEQ ID NO: 4.

The pharmaceutical composition of the present invention was intraperitoneally administered into a CLP mouse to confirm an antiinflammatory effect thereof. Specifically, the CLP mouse was anesthetized by administering pentothal sodium (50 mg/kg) intraperitoneally, and then its abdomen was dissected to expose the cecum. The cecum was ligated below the ileocecal valve, punctured twice with a 22-gauge needle, and then the abdomen was closed.

The amino acid sequence of SEQ ID NO: 4 was prepared based on SH3-1 and SH3-2 sequences related to p67phox and p47phox, which are components of NADPH oxidase, in a c-Src sequence (FIG. 1). Simply, the amino acid sequence of SEQ ID NO: 4 was combined and deduced by researching a sequence that exhibits the highest antiinflammatory effect without linkage of a SH3-1 sequence and a SH3-2 sequence.

In the present invention, the β-1,3-glucan and the peptide may be linked by a spacer, but the present invention is not limited thereto. The spacer is a part linking an SPG sequence and an SH3 peptide sequence into one sequence, and may be a peptide including a sequence of 1 to 10 amino acids. More preferably, the spacer is a sequence of 3 to 7 amino acids, and most preferably, a sequence of 4 to 5 amino acids.

The amino acid sequence of the spacer may consist of a repeat of the same amino acid, and most preferably, includes a repeat of glycine (G).

In the present invention, the β-1,3-glucan may be SPG. The SPG may be obtained from *Schizophyllum commune*, but the present invention is not limited thereto.

In the present invention, the composition may further include an antibiotic. One or more antibiotics may be included, and two or more antibiotics may be included in the same ratio.

An infection causing sepsis is a bacterial infection generally caused by gram-positive bacteria or gram-negative bacteria, but may be infections caused by fungi or viruses. The antibiotic of the present invention may include one or more selected from the group consisting of cephalosporins, β-lactam antibiotics, β-lactam/β-lactamase inhibitor antibiotics, quinolone antibiotics, glycopeptide antibiotics, carbapenem antibiotics, aminoglycoside antibiotics, macrolide antibiotics, sulfa drug antibiotics, aztreonam, clindamycin, tigecycline, colistin sodium methanesulfonate, metronidazole and spiramycin, and most preferably, is selected from cephalosporins and aminoglycoside antibiotics.

The cephalosporins may include one or more selected from the group consisting of cefazolin, cefcapene pivoxil, cefpodoxime proxetil, cephradine, ceftriaxone, cefbuperazone, cefotaxime, cefminox, ceftazidime, cefpirome, cefixime, cephalexin, cefdinir, cefroxadine, cefuroxime, cefadroxil, cefoxitin, cefetamet pivoxil, ceftizoxime, cefamandole nafate, cefazedone, cefteram pivoxil, ceftezole, cefprozil, cefotetan, cefmenoxime, cefditoren pivoxil, cefatrizine propylene glycol, cefotiam, cefotiam hexetil hydrochloride, ceftibuten, cefaclor, cefoperazone, cefpiramide, cephalothin, cefodizime, cefonicid, cefmetazole and cefepime;

the β-lactam antibiotics may include one or more selected from the group consisting of nafcillin, piperacillin and ampicillin;

the β-lactamase inhibitor antibiotics may include any one or more selected from the group consisting of sulbactam, tazobactam, sultamicillintosylate, amoxicillin, potassium clavulanate, ticarcillin and pivoxyl sulbactam;

the quinolone antibiotics may include any one or more selected from the group consisting of ciprofloxacin, moxifloxacin, levofloxacin and lomefloxacin;

the glycopeptide antibiotics may include any one or more selected from the group consisting of vancomycin, linezolid and teicoplanin;

the carbapenem antibiotics may include any one or more selected from the group consisting of meropenem, doripenem monohydrate, cilastatin and imipenem monohydrate;

the aminoglycoside antibiotics may include any one or more selected from the group consisting of amikacin, tobramycin, netilmicin, sisomicin, isepamicin, fosfomycin and gentamicin;

the macrolide antibiotics may include any one or more selected from the group consisting of clarithromycin, roxithromycin and azithromycin;

the aztreonam may be a monobactam antibiotic; and the sulfa drug antibiotics may include any one or more selected from the group consisting of sulfamethoxazole and trimethoprim, but the present invention is not limited thereto.

These antibiotics may be used in combination once or more with any one or more substances selected from the group consisting of sodium, hydrochloric acid (HCl), sodium chloride (NaCl), sulfates and phosphates.

The composition of the present invention may reduce ROS produced when an inflammatory disease occurs, and ROS is known to be largely produced during mitochondrial respiration and macrophage-mediated phagocytosis. When the β-glucan-peptide complex of the present invention is used in combination with one of the antibiotics, particularly, ROS produced by a phagocyte may be specifically reduced. Therefore, an inflammation inhibitory effect caused by the inhibition of ROS caused by a phagocyte, not ROS produced by mitochondria, may be more clearly described. The phagocyte may be any one or more selected from the group consisting of a macrophage, a dendritic cell, a monocyte, a mast cell and a neutrophil, and more preferably, a macrophage, a dendritic cell and a neutrophil, and most preferably, a macrophage, but the present invention is not limited thereto.

The composition of the present invention may significantly reduce an expression level of an inflammatory cytokine, other than ROS (FIG. 5), and significantly increase a survival rate (FIG. 4) of a rat with sepsis induced by CLP and an antibacterial effect (FIG. 6) on sepsis bacteria, thereby exhibiting an effect of preventing or treating an inflammatory disease such as sepsis.

The inflammatory disease of the present invention may be any one or more selected from the group consisting of sepsis, septic shock, inflammatory bowel disease (IBD), peritonitis, nephritis, acute bronchitis, chronic bronchitis, osteoarthritis, bowel disease spondylitis, chronic obstructive pulmonary disease (COPD), rheumatoid arthritis, acute lung injury and broncho-pulmonary dysplasia, and more preferably, sepsis, septic shock, COPD, an acute lung injury and broncho-pulmonary dysplasia, and most preferably, sepsis.

In addition, the present invention provides a health functional food composition, which includes β-1,3-glucan; and a peptide consisting of an amino acid sequence of SEQ ID NO: 4 for use in the prevention or alleviation of an inflammatory disease. The β-1,3-glucan and the peptide consisting of an amino acid sequence of SEQ ID NO: 4 may be the same as those used in the pharmaceutical composition, and therefore, descriptions thereof will be omitted.

The food composition according to the present invention may be prepared in various forms according to a conventional method known in the art. Common foods may be manufactured by adding the β-glucan-peptide complex of the present invention to beverages (including an alcoholic beverage), fruits and processed foods thereof (e.g., fruit canned food, bottled food, jam and marmalade), fish, meat and processed foods thereof (e.g., ham, sausage, and corned beef), bread and noodles (e.g., udon, buckwheat noodles, ramen, spaghetti and macaroni), juice, various drinks, cookies, syrup, dairy products (e.g., butter and cheese), edible vegetable oil, margarine, vegetable protein, retort food, frozen food, various types of seasonings (e.g., bean paste, soy sauce and other sauces), but the present invention is not limited thereto. In addition, nutritional supplements may be manufactured by adding the β-glucan-peptide complex of the present invention to a capsule, tablet or pill, but the present invention is not limited thereto. In addition, as the health functional food, the β-glucan-peptide complex of the present invention itself may be manufactured in the form of tea, juice and drink and thus ingested (as a health drink) after liquefaction, granulation, encapsulation, and powdering, but the present invention is not limited thereto. In addition, to use the β-glucan-peptide complex in the form of a food additive, the peptide complex may be manufactured in the form of a powder or concentrate. In addition, the β-glucan-peptide complex of the present invention may be mixed with an active component known to have an effect of preventing and alleviating an inflammatory disease, thereby preparing a composition.

When the β-glucan-peptide complex of the present invention is used as a health drink, the health drink composition may contain various flavors or natural carbohydrates as additional components like a conventional beverage. The above-mentioned natural carbohydrates may include monosaccharides such as glucose and fructose; disaccharides such as maltose and sucrose; polysaccharides such as dextrin and cyclodextrin; and sugar alcohols such as xylitol, sorbitol and erythritol. Sweeteners may include natural sweeteners such as taumatin and a stevia extract; and synthetic sweeteners such as saccharin and aspartame. Generally, the proportion of the natural carbohydrates is approximately 0.01 to 0.04 g, and preferably, approximately 0.02 to 0.03 g per 100 mL of the composition of the present invention.

In addition, the β-glucan-peptide complex of the present invention may contain a food composition for preventing and alleviating an inflammatory disease as an active ingredient, and its content may be an effective amount to achieve prevention and alleviation of an inflammatory disease, and is preferably 0.01 to 100 wt % with respect to the total weight of the composition, but the present invention is not particularly limited thereto. The food composition of the present invention may be prepared by mixing the β-glucan-peptide complex with another active ingredient known to have an effect in a composition for preventing and alleviating an inflammatory disease.

Other than these, the health food of the present invention may contain various nutrients, vitamins, electrolytes, flavors, colorants, pectic acids, salts of pectic acids, alginic acids, salts of alginic acids, organic acids, protective colloidal thickening agents, pH adjusters, stabilizers, preservatives, glycerin, alcohols or carbonating agents. In addition, the health food of the present invention may contain fruit pulp to prepare a natural fruit juice, a fruit juice drink or a vegetable drink. Such components may be used independently or in combination. The proportion of additives may be, but is not very important, generally selected in a range of 0.01 to 0.1 parts by weight of 100 parts by weight of the composition of the present invention.

In addition, the present invention provides an antiinflammatory composition, which includes β-1,3-glucan; and peptide consisting of an amino acid sequence of SEQ ID NO: 4. The β-1,3-glucan and the peptide consisting of an amino acid sequence of SEQ ID NO: 4 are the same as those used in the pharmaceutical composition, and thus descriptions thereof are omitted.

The composition may be any one or more selected from the group consisting of a food composition, a cosmetic composition and a pharmaceutical composition, but the present invention is not limited thereto.

In addition, the present invention provides an antiinflammatory composition effective against sepsis-causing bacteria, which includes β-1,3-glucan; a peptide consisting of an amino acid sequence of SEQ ID NO: 4; and an antibiotic. The β-1,3-glucan, the peptide consisting of an amino acid sequence of SEQ ID NO: 4 and the antibiotic are the same as those used in the pharmaceutical composition, and thus descriptions thereof are omitted.

The sepsis-causing bacteria may include *Streptococcus, Staphylococcus, Escherichia coli,* Pneumococcus, *Pseudomonas aeruginosa* and fungi, and may be microorganisms such as bacteria, viruses or fungi, which cause symptoms of sepsis, but the present invention is not limited thereto.

In addition, the present invention provides a method of preventing or treating an inflammatory disease, which includes administering β-1,3-glucan and a peptide consisting of an amino acid sequence of SEQ ID NO: 4 to a patient. Since the β-1,3-glucan and the peptide consisting of an amino acid sequence of SEQ ID NO: 4 are the same as those used in the pharmaceutical composition, descriptions thereof are omitted. The inflammatory disease is the same as a target of the pharmaceutical composition, and thus descriptions thereof are omitted.

The method may further include administering an antibiotic to a patient. The administration of the antibiotic includes simultaneously or sequentially administering β-1,3-glucan and a peptide consisting of an amino acid sequence of SEQ ID NO: 4.

Advantageous Effects

Accordingly, when β-1,3-glucan and a peptide consisting of an amino acid sequence of SEQ ID NO: 4 are included, since the level of reactive oxygen species (ROS), sepsis-causing bacteria or an inflammatory cytokine of a sepsis mouse can be lowered, and the survival rate of the mouse can be significantly increased, they are effective for use in a composition or method for preventing, alleviating or treating an inflammatory disease such as sepsis. Particularly, the ROS generated by a phagocyte is specifically reduced and when used in combination with an antibiotic, ROS, sepsis-causing bacteria or the expression level of an inflammatory cytokine can be significantly decreased, thereby significantly increasing a survival rate, resulting in a more excellent effect.

DESCRIPTION OF DRAWINGS

FIG. 1 shows a c-Src sequence and SH3-1 and SH3-2 sequences that can be obtained therefrom, and p67phox and p47phox sequences.

MODES OF THE INVENTION

Example 1

Experiment Preparation

<1-1> Cells and CLP Mice

A mouse macrophage cell line, which is RAW2647 (ATCCTIB-71; American Type Culture Collection) cells, was cultured using DMEM (Invitrogen) containing 10% fetal bovine serum (FBS; Invitrogen), sodium pyruvate, non-essential amino acids, penicillin G (100 IU/ml) and streptomycin (100 μg/ml).

Sepsis mouse models induced by cecal ligation and puncture (CLP) were prepared using 6-week-old C57BL/6 female mice (Samtako, Korea). All animal-related procedures were approved by the Institutional Animal Care and Use Committee of Hanyang University. The CLP mice were intraperitoneally administered three times (at 3, 6 and 12 hours) with an administered substance shown in Table 1. SPG-SC is a peptide complex having a sequence in which SPG-SH3 sequences were randomly mixed, and as the antibiotic, a combination of gentamycin and cephalosporin was used.

TABLE 1

| Administered substance | Dose |
|---|---|
| PBS | 10 mg/kg |
| SPG-SC | 10 mg/kg |

TABLE 1-continued

| Administered substance | Dose |
|---|---|
| SPG-SH3 | 10 mg/kg |
| SPG-SH3 + Antibiotics (Gentamycin + Cephalosporin) | 10 mg/kg + (8 mg/kg + 8 mg/kg) |
| Antibiotics (Gentamycin + Cephalosporin) | 8 mg/kg + 8 mg/kg |

<1-2> Preparation of SPG-SH3

A SH3 peptide sequence was prepared from a SH3-1 sequence and a SH3-2 sequence, which were derived from the c-Src sequence. A scramble (SC) sequence was prepared of amino acids which are not included in a SH3 sequence of the SH3-1 sequence and the SH3-2 sequence. The sequences are shown in Table 2 below.

To prepare an SPG-SH3 complex, β-1,3-glucan was dissolved in an organic solvent, and then a cyclic anhydride was added thereto, such that a hydroxyl group of the β-1,3-glucan was converted into a carboxyl group (—COOH group). Afterward, a β-glucan-peptide complex, SPG-SH3, was prepared by linking the carboxyl group with each of an amine group of a SH3-1, SH3-2 or SH3 peptide.

TABLE 2

| Peptide | Sequence | SEQ ID NO: |
|---|---|---|
| c-Src | GGVTTFVALY DTESRTETDL SFKKGERLQI VNNTEGDWWL AHSLSTGQTG YIPSNYVAPS DS | 1 |
| SH3-1 | ALYDYESRTE TDLSFKKG | 2 |
| SH3-2 | WWLAHSLSTG QTGYIPSNYV | 3 |
| SH3 | ALLSFKKGGQ TGYIPSNYV | 4 |
| SC | YDYESRTETD WWLAHSLST | 5 |

Example 2

ROS Production Inhibitory Effect of SPG-SH3 (In Vitro)

Whether reactive oxygen species (ROS) production is inhibited when RAW2647 cells were treated with each of SPG-SH1, SPG-SH2 or SPG-SH3 was determined. Particularly. NADPH oxidase (NOX) activity and a mitochondrial ROS level were confirmed.

Particularly, after the RAW2647 cells were stimulated with LPS, SPG-SH1, SPG-SH2 or SPG-SH3 was treated at a concentration of 1, 5 or 10 μg/mL, respectively. The NADPH oxidase activity was confirmed by measuring the production of a superoxide in the RAW2647 cells by a lucigenin (bis-N-methylacridinium nitrate)-ECL method. The production of mitochondrial ROS was determined by staining the RAW2647 cells with 5 μM of MitoSOX for 30 minutes and then measuring mean fluorescence intensity (MFI) by FACS analysis.

Figure 2:
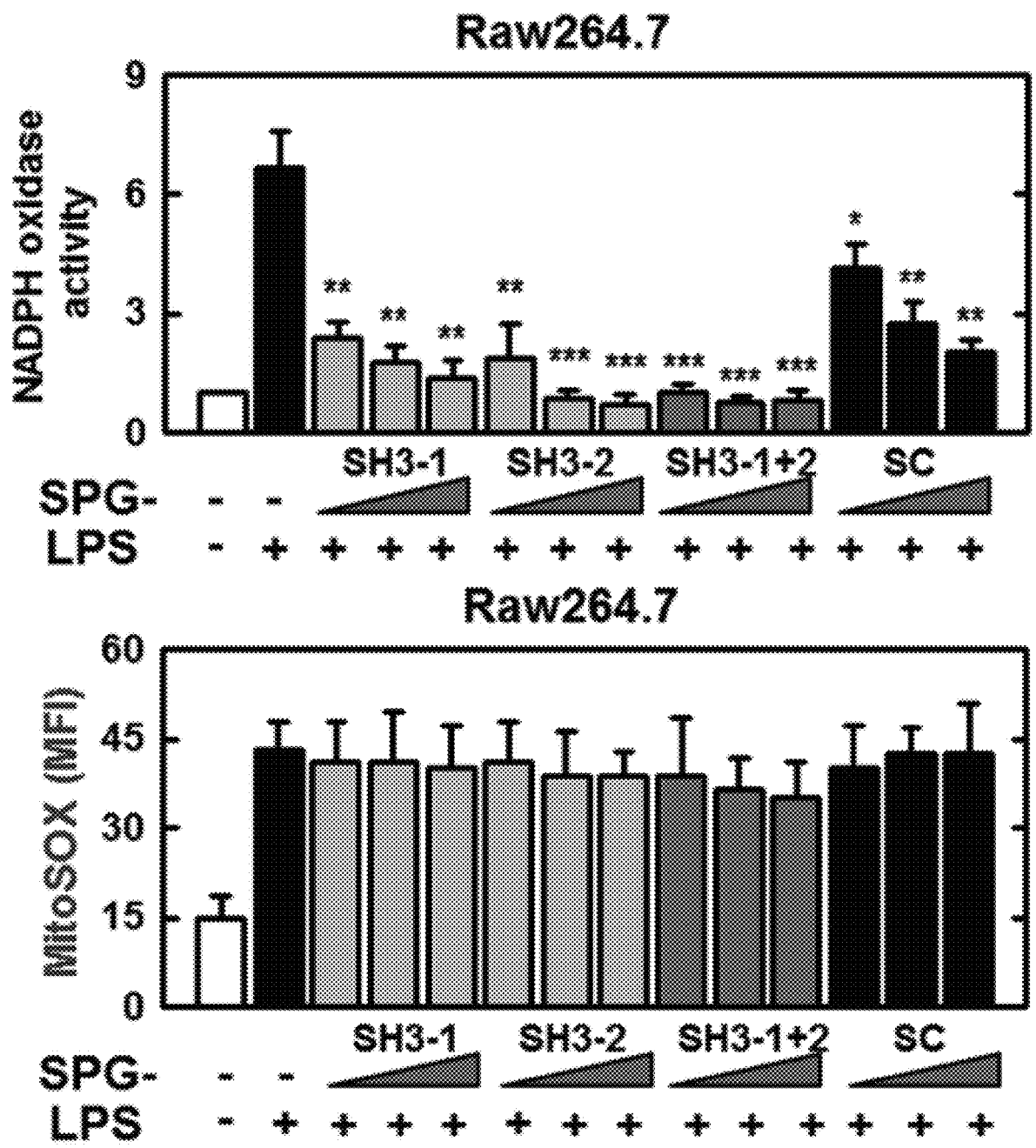
FIG. 2 shows the result of measuring the activity of NADPH oxidase or a mitochondrial reactive oxygen species (ROS) (MitoSOX) level after RAW2647 cells are treated with LPS, and with SH3-1, SH3-2, SH3 (SH3-1+SH3-2) or SC at a different concentration (1, 5 or 10 μg/mL). A control is not treated. It can be confirmed that a NADPH oxidase activity level is the lowest when SH3 is treated, and the mitochondrial ROS level (MitoSOX) indicates that ROS is produced at a similar level regardless of a treated substance.

As a result, as shown in FIG. 2, it can be confirmed that the NADPH oxidase activity was the lowest when SPG-SH3 was treated, but the mitochondrial ROS was produced at a similar level regardless of the type of an administered substance.

Example 3

ROS Production Inhibitory Effect of SPG-SH3 and Antibiotic (In Vivo)

Whether ROS production was inhibited when a CLP mouse was co-treated with SPG-SH3 and an antibiotic was determined. Particularly, NADPH oxidase (NOX) activity, total ROS and a mitochondrial ROS level were confirmed.

Particularly, CLP mice (n=5) treated with the same administered substances as in Example <1-1> were prepared. The measurement of the NADPH oxidase activity was confirmed by acquiring and fractionating the spleen of the CLP mice and measuring the NADPH oxidase activity in the same manner as in Example 2. Total ROS was confirmed by acquiring and fractionating the spleen of the CLP mice and measuring excitation wavelength/emission wavelength (Ex/Em) at 490/525 nm after a 5 μM reagent in a total ROS activity assay kit (CA-R900) was treated for 60 minutes. The production of mitochondrial ROS was confirmed by acquiring and fractionating the spleen of the CLP mice and measuring the production of mitochondrial ROS in the same manner as in Example 2. Alternatively, the spleen of the CLP mouse was obtained and fractionated, a 5 μM reagent in a mitochondrial ROS activity assay kit (CA-R933) was treated for 60 minutes, and Ex/Em was measured at 490/525 nm. As a control (UN), a normal mouse was treated with a vehicle.

Figure 3:
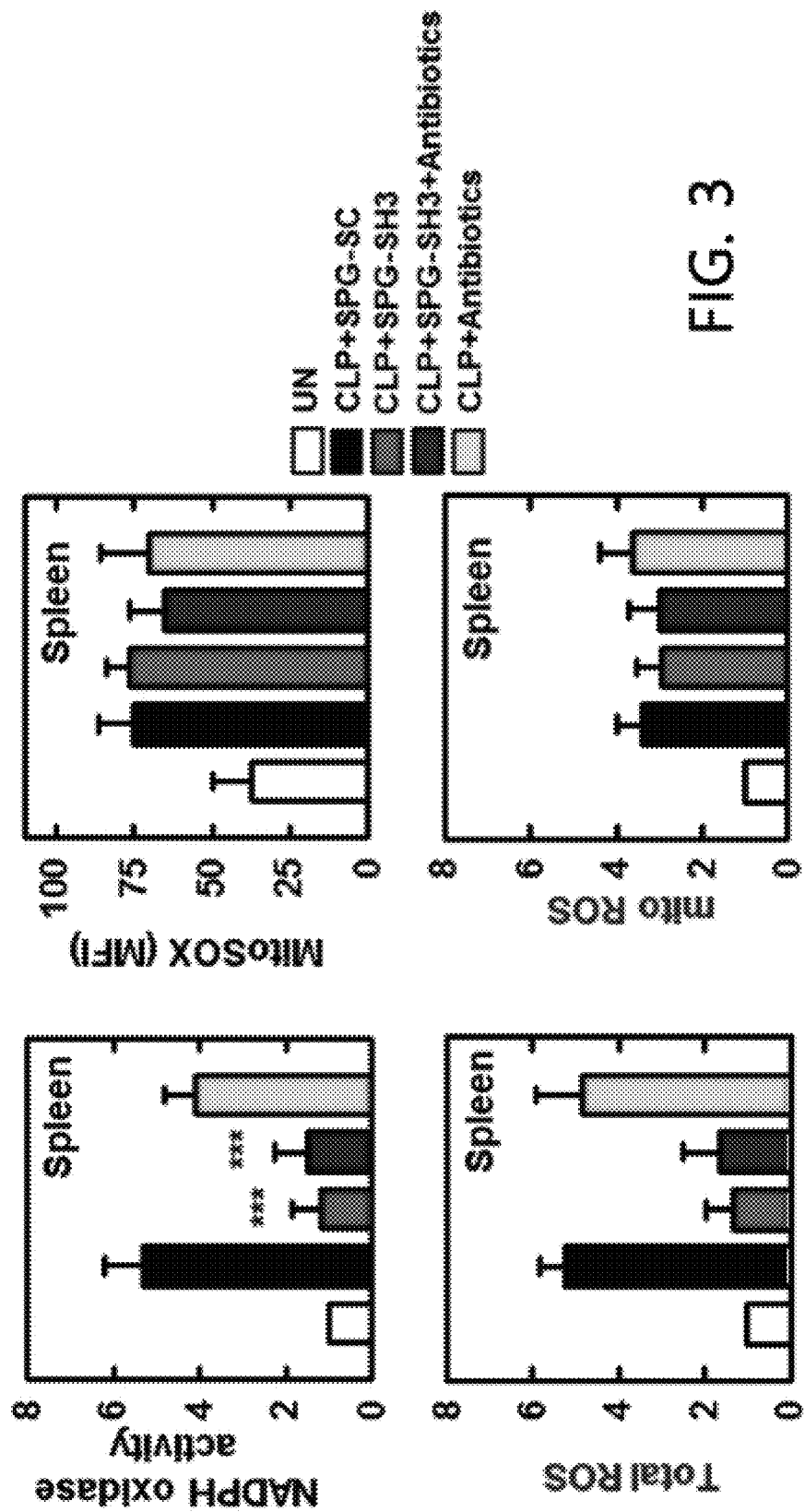
FIG. 3 shows the NADPH oxidase activity, and total ROS and mitochondrial ROS levels measured in the spleen of a CLP mouse after the CLP mouse is treated with SPG-SC, SPG-SH3, an antibiotic or a combination of SPG-SH3 and an antibiotic. A control is not treated. It can be confirmed that the NADPH oxidase activity level and the total ROS level are significantly reduced when SPG-SH3 and the combination of SPG-SH3 and an antibiotic are treated, and the mitochondrial ROS level indicates that ROS is produced at a similar level regardless of a treated substance.

As a result, as shown in FIG. 3, it can be confirmed that the NADPH oxidase activity or total ROS level was significantly reduced when SPG-SH3 or a combination of SPG-SH3 and an antibiotic was treated. On the other hand, it can be confirmed that mitochondria continuously produced ROS at a similar level regardless of the type of an administered substance.

That is, the results of Examples 2 and 3 indicate that the SPG-SH3 of the present invention targets a phagocyte such as a macrophage, a dendritic cell or a neutrophil, not mitochondria among the causes of ROS production to reduce ROS production.

Example 4

Protective Effect of SPG-SH3 and Antibiotic

Whether a protective effect was exhibited in a mouse having systemic sepsis induced by CLP when the SPG-SH3 of the present invention and a combination of SPG-SH3 and an antibiotic were used was determined by measuring a death rate.

Specifically. CLP mice (n=7, twice; total 14) were treated with the administered substances as in Example <1-1> and monitored for 7 days.

Figure 4:
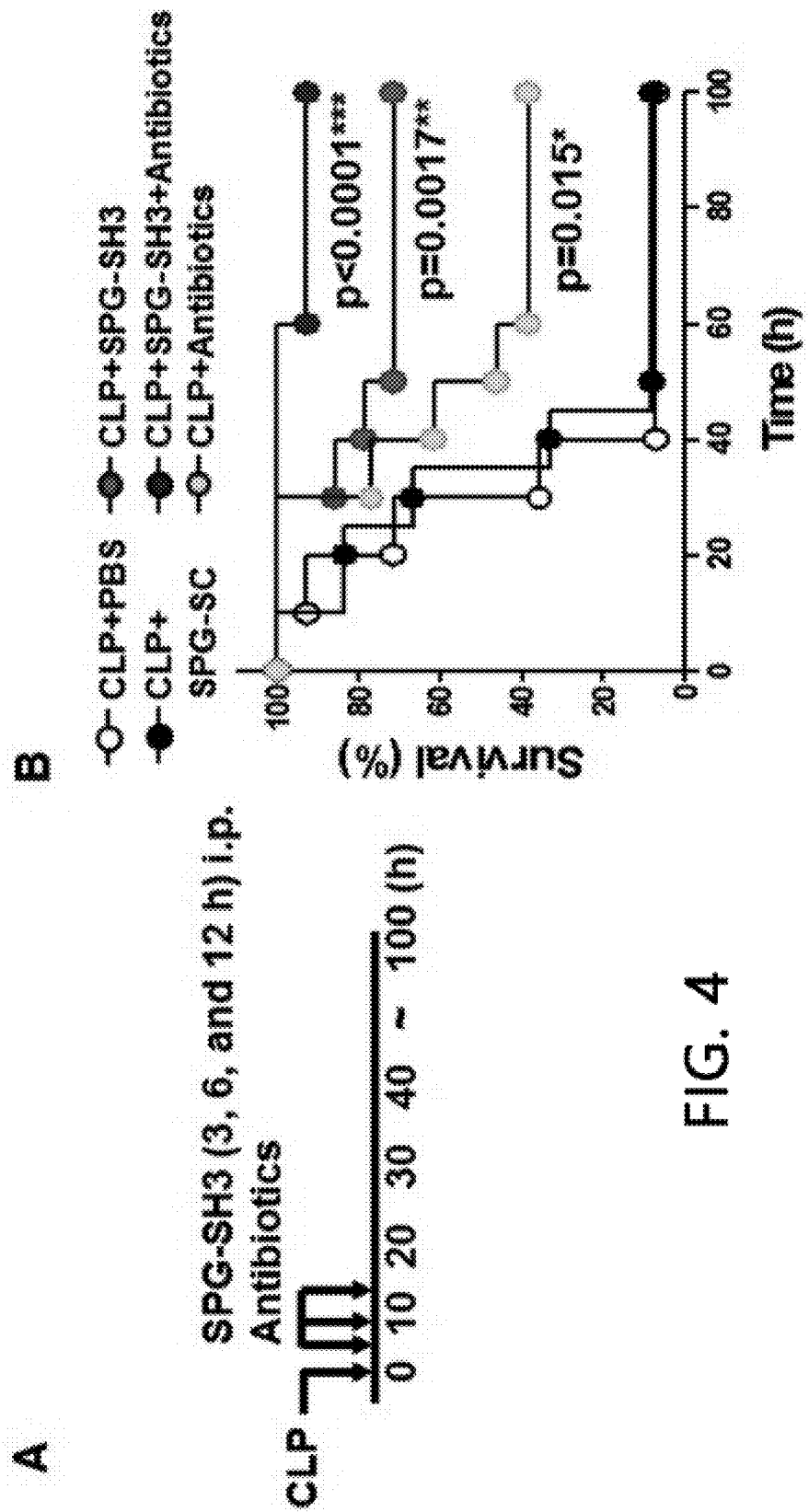
FIG. 4 shows the result of confirming the survival rate of a CLP mouse for 7 days after the CLP mouse is treated with SPG-SC, SPG-SH3, an antibiotic or a combination of SPG-SH3 and an antibiotic. When the combination of SPG-SH3 and an antibiotic is treated, due to a synergistic effect, it can be confirmed that approximately 90% of the CLP mice are survived.

As a result, as shown in FIG. 4, approximately 60 hours after the mice were subjected to CLP treatment, the SPG-SH3-treated group only showed a survival rate of approximately 70%, and the antibiotic-treated group only showed a survival rate of approximately 40%. On the other hand, it was confirmed that the SPG-SH3+antibiotic-treated group had a synergistic effect, thereby showing the highest survival rate of 90%.

Example 5

Antiinflammatory Effect of SPG-SH3 and Antibiotic

Whether a pro-inflammatory cytokine was inhibited when CLP mice were treated with a combination of SPG-SH3 and an antibiotic was determined.

Specifically, 20 hours after CLP mice were treated with the same administered substances as in Example <1-1>, the peripheral blood was obtained. The concentrations of TNF-α, IL-6, IL-1β and IL-18 in the blood were measured using an ELISA kit (BD Biosciences).

Figure 5:
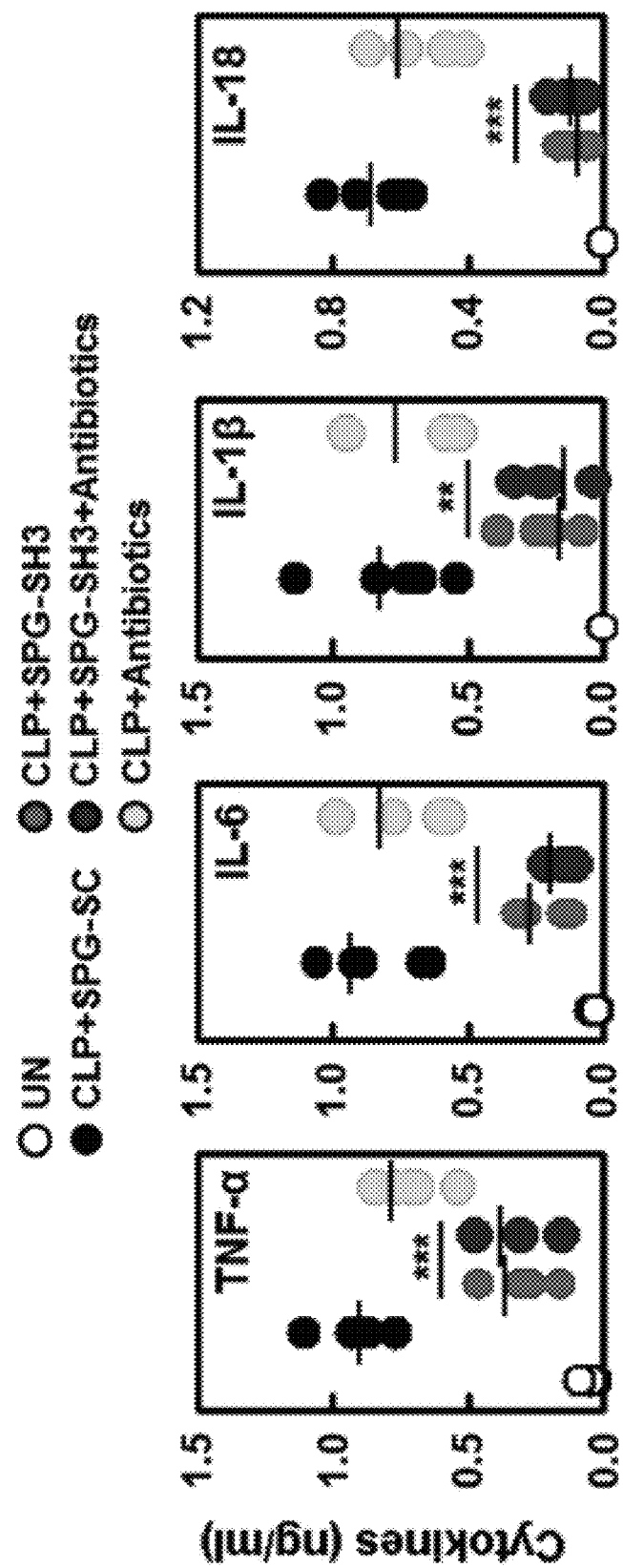
FIG. 5 shows the expression levels of inflammatory cytokines such as TNF-α, IL-6, IL-1β and IL-18 after CLP mice are treated with SPG-SC, SPG-SH3, an antibiotic and a combination of SPG-SH3 and an antibiotic. It can be confirmed that when SPG-SH3 and a combination of SPG-SH3 and an antibiotic are treated, the inflammatory cytokine levels are significantly reduced.

As a result, as shown in FIG. 5, it can be confirmed that the concentrations of TNF-α, IL-6, IL-1β and IL-18 were significantly reduced when SPG-SH3 or a combination of SPG-SH3 and an antibiotic was treated.

Example 6

Antibacterial Effect of SPG-SH3 and Antibiotic

CLP-induced sepsis is associated with bacteria in the peripheral blood or peritoneal fluid. Therefore, when a CLP mouse was treated with a combination of SPG-SH3 and an antibiotic, it was intended to determine an antibacterial effect against bacteria.

Specifically, the peripheral blood and the peritoneal fluid were obtained 20 hours after CLP mice were treated with the same administered substance as in Example <1-1>. 5 μL each of the peripheral blood and the peritoneal fluid was spotted on a blood agar plate, and then incubated in a 37° C. incubator for 18 hours, followed by colony-forming unit (CFU) measurement.

Figure 6:
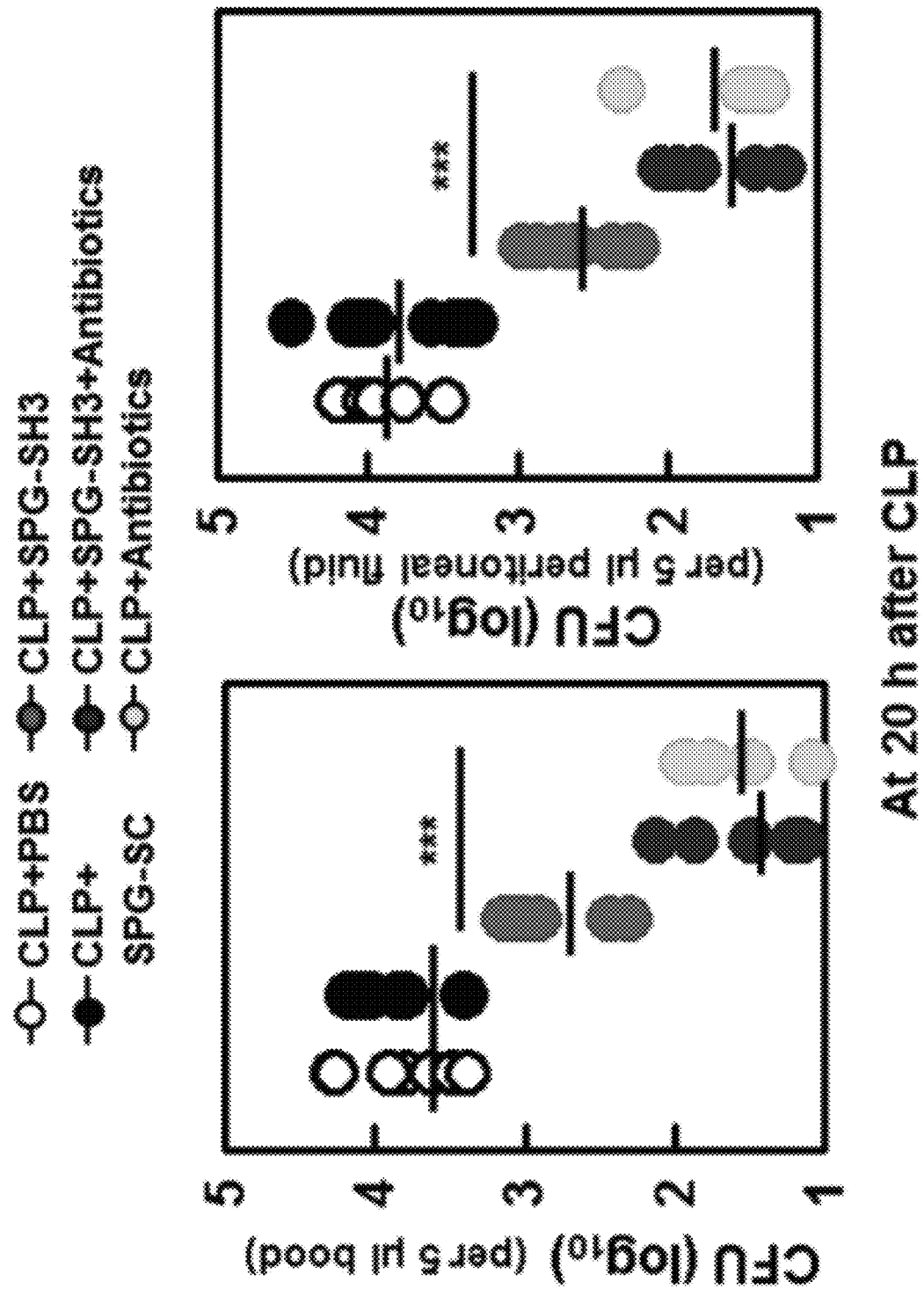
FIG. 6 shows the antibacterial effect by measuring the level of sepsis-causing bacteria in the peripheral blood or peritoneal fluid after a CLP mouse is treated with SPG-SC, SPG-SH3, an antibiotic or a combination of SPG-SH3 and an antibiotic. It can be confirmed that when the combination of SPG-SH3 and an antibiotic is treated, sepsis-causing bacteria are significantly reduced.

As a result, as shown in FIG. 6, it can be confirmed that the CFU was significantly reduced in the peripheral blood or peritoneal fluid. Particularly, in the peritoneal fluid, the treatment of the combination of SPG-SH3 and an antibiotic led to the most excellent antibacterial effect.

INDUSTRIAL APPLICABILITY

Since β-1,3-glucan and a peptide consisting of an amino acid sequence of SEQ ID NO: 4, which are provided by the present invention, lead to an excellent ROS production inhibitory effect or an excellent antiinflammatory effect, and an excellent protective effect in a sepsis model or an excellent antibacterial effect against sepsis bacteria, they can be effectively used in a composition, antiinflammatory composition or antibacterial composition for preventing, alleviating or treating an inflammatory disease, and a method of preventing or treating an inflammatory disease, resulting in high industrial availability.

SEQUENCE LISTING FREE TEXT

SEQ ID NO: 1 is a c-Src sequence, consisting of 62 amino acids.

SEQ ID NO: 2 is a SH3-1 sequence, consisting of 18 amino acids.

SEQ ID NO: 3 is a SH3-2 sequence, consisting of 20 amino acids.

SEQ ID NO: 4 is a SH3 sequence, consisting of 19 amino acids.

SEQ ID NO: 5 is a scramble (SC) sequence, consisting of 19 amino acids.

The invention claimed is:

1. A pharmaceutical composition for use in the treatment of an inflammatory disease, comprising: a β-1,3-glucan; and a peptide consisting of the amino acid sequence of SEQ ID NO: 4.

2. The pharmaceutical composition of claim 1, wherein said β-1,3-glucan and said peptide are linked by a spacer.

3. The pharmaceutical composition of claim 2, wherein said spacer is a peptide including a GGGG amino acid sequence, wherein G is glycine.

4. The pharmaceutical composition of claim 1, wherein said β-1,3-glucan is schizophyllan (SPG).

5. The pharmaceutical composition of claim 1, further comprising an antibiotic.

6. The pharmaceutical composition of claim 5, wherein said antibiotic includes one or more selected from the group consisting of cephalosporins, β-lactam antibiotics, β-lactam/β-lactamase inhibitor antibiotics, quinolone antibiotics, glycopeptide antibiotics, carbapenem antibiotics, aminoglycoside antibiotics, macrolide antibiotics, monobactam antibiotics, sulfa drug antibiotics, aztreonam, clindamycin, tigecycline, colistin sodium methanesulfonate, metronidazole and spiramycin.

7. The pharmaceutical composition of claim 6, wherein said cephalosporins include one or more selected from the group consisting of cefazolin, cefcapene pivoxil, cefpodoxime proxetil, cephradine, ceftriaxone, cefbuperazone, cefotaxime, cefminox, ceftazidime, cefpirome, cefixime, cephalexin, cefdinir, cefroxadine, cefuroxime, cefadroxil, cefoxitin, cefetamet pivoxil, ceftizoxime, cefamandole nafate, cefazedone, cefteram pivoxil, ceftezole, cefprozil, cefotetan, cefmenoxime, cefditoren pivoxil, cefatrizine propylene glycol, cefotiam, cefotiam hexetil hydrochloride, ceftibuten, cefaclor, cefoperazone, cefpiramide, cephalothin, cefodizime, cefonicid, cefmetazole and cefepime; wherein:

said β-lactam antibiotics include one or more selected from the group consisting of nafcillin, piperacillin and ampicillin;
said β-lactamase inhibitor antibiotics include one or more selected from the group consisting of sulbactam, tazobactam, sultamicillintosylate, amoxicillin, potassium clavulanate, ticarcillin and pivoxyl sulbactam;
said quinolone antibiotics include one or more selected from the group consisting of ciprofloxacin, moxifloxacin, levofloxacin and lomefloxacin;
said glycopeptide antibiotics include one or more selected from the group consisting of vancomycin, linezolid and teicoplanin;
said carbapenem antibiotics include one or more selected from the group consisting of meropenem, doripenem monohydrate, cilastatin and imipenem monohydrate;
said aminoglycoside antibiotics include one or more selected from the group consisting of amikacin, tobramycin, netilmicin, sisomicin, isepamicin, fosfomycin and gentamicin;
said macrolide antibiotics include one or more selected from the group consisting of clarithromycin, roxithromycin and azithromycin; and
said sulfa drug antibiotics include one or more selected from the group consisting of sulfamethoxazole and trimethoprim.

8. The pharmaceutical composition of claim 1, which reduces reactive oxygen species (ROS) production of any one or more phagocytes selected from the group consisting of a macrophage, a dendritic cell, a monocyte, a mast cell, and a neutrophil.

9. The pharmaceutical composition of claim 1, wherein said inflammatory disease includes one or more selected from the group consisting of sepsis, septic shock, inflammatory bowel disease (IBD), peritonitis, nephritis, acute bronchitis, chronic bronchitis, osteoarthritis, bowel disease spondylitis, chronic obstructive pulmonary disease (COPD), rheumatoid arthritis, acute lung injury and broncho-pulmonary dysplasia.

10. A health functional food composition for use in the alleviation of an inflammatory disease, comprising:
a β-1,3-glucan; and
a peptide consisting of the amino acid sequence of SEQ ID NO: 4.

11. An anti-inflammatory composition, comprising:
a β-1,3-glucan; and
a peptide consisting of the amino acid sequence of SEQ ID NO: 4.

12. An antibacterial composition for use against sepsis-causing bacteria, comprising:
a β-1,3-glucan;
a peptide consisting of the amino acid sequence of SEQ ID NO: 4; and
an antibiotic.

13. A method of treating an inflammatory disease, comprising:
administering a β-1,3-glucan and a peptide consisting of the amino acid sequence of SEQ ID NO: 4 to a patient in need thereof.

14. The method of claim 13, wherein said β-1,3-glucan and said peptide are linked by a spacer.

15. The method of claim 14, wherein said spacer is a peptide comprising the amino acid sequence GGGG, wherein G is glycine.

16. The method of claim 13, wherein said β-1,3-glucan is schizophyllan (SPG).

17. The method of claim 13, further comprising:
administering an antibiotic to a patient in need thereof.

18. The method of claim 17, wherein said antibiotic includes one or more selected from the group consisting of cephalosporins, β-lactam antibiotics, β-lactam/β-lactamase inhibitor antibiotics, quinolone antibiotics, glycopeptide antibiotics, carbapenem antibiotics, aminoglycoside antibiotics, macrolide antibiotics, sulfa drug antibiotics, aztreonam, clindamycin, tigecycline, colistin sodium methanesulfonate, metronidazole and spiramycin.

19. The method of claim 18, wherein said cephalosporin antibiotics include one or more selected from the group consisting of cefazolin, cefcapene pivoxil, cefpodoxime proxetil, cephradine, ceftriaxone, cefbuperazone, cefotaxime, cefminox, ceftazidime, cefpirome, cefixime, cephalexin, cefdinir, cefroxadine, cefuroxime, cefadroxil, cefoxitin, cefetamet pivoxil, ceftizoxime, cefamandole nafate, cefazedone, cefteram pivoxil, ceftezole, cefprozil, cefotetan, cefmenoxime, cefditoren pivoxil, cefatrizine propylene glycol, cefotiam, cefotiam hexetil hydrochloride, ceftibuten, cefaclor, cefoperazone, cefpiramide, cephalothin, cefodizime, cefonicid, cefmetazole and cefepime;

said β-lactam antibiotics include one or more selected from the group consisting of nafcillin, piperacillin and ampicillin;

said β-lactamase inhibitor antibiotics include one or more selected from the group consisting of sulbactam, tazobactam, sultamicillintosylate, amoxicillin, potassium clavulanate, ticarcillin and pivoxyl sulbactam;

said quinolone antibiotics include one or more selected from the group consisting of ciprofloxacin, moxifloxacin, levofloxacin and lomefloxacin;

said glycopeptide antibiotics include one or more selected from the group consisting of vancomycin, linezolid and teicoplanin;

said carbapenem antibiotics include one or more selected from the group consisting of meropenem, doripenem monohydrate, cilastatin and imipenem monohydrate;

said aminoglycoside antibiotics include one or more selected from the group consisting of amikacin, tobramycin, netilmicin, sisomicin, isepamicin, fosfomycin and gentamicin;

said macrolide antibiotics include one or more selected from the group consisting of clarithromycin, roxithromycin and azithromycin; and said sulfa drug antibiotics include one or more selected from the group consisting of sulfamethoxazole and trimethoprim.

20. The method of claim 13, wherein said inflammatory disease includes one or more selected from the group consisting of sepsis, septic shock, inflammatory bowel disease (IBD), peritonitis, nephritis, acute bronchitis, chronic bronchitis, osteoarthritis, bowel disease spondylitis, chronic obstructive pulmonary disease (COPD), rheumatoid arthritis, acute lung injury and broncho-pulmonary dysplasia.

* * * * *